United States Patent
Kluckner et al.

(10) Patent No.: US 10,049,301 B2
(45) Date of Patent: Aug. 14, 2018

(54) MEDICAL SCANNER TEACHES ITSELF TO OPTIMIZE CLINICAL PROTOCOLS AND IMAGE ACQUISITION

(71) Applicant: Siemens Healthcare GmbH, Erlangen (DE)

(72) Inventors: Stefan Kluckner, Lawrenceville, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 16 days.

(21) Appl. No.: 15/224,710

(22) Filed: Aug. 1, 2016

(65) Prior Publication Data

US 2018/0032841 A1 Feb. 1, 2018

(51) Int. Cl.
*G06K 9/00* (2006.01)
*G06K 9/62* (2006.01)
*G16H 40/63* (2018.01)

(52) U.S. Cl.
CPC .............. *G06K 9/6263* (2013.01); *G06K 9/00* (2013.01); *G06K 9/6265* (2013.01); *G16H 40/63* (2018.01)

(58) Field of Classification Search
CPC .... A61B 2034/2055; A61B 2090/3735; A61B 2090/378; A61B 8/00; A61B 17/00; A61B 2017/00398; A61B 2090/363; A61B 2090/364; A61B 2090/3916; A61B 2090/3954; A61B 2090/3966; A61B 2090/3991; A61B 2034/104; A61B 2034/105; A61B 2034/107; A61B 2090/103; A61B 34/10; A61B 5/055; A61B 5/4566; A61B 2034/101; A61B 2034/2057; A61B 2034/252; A61B 2034/254; A61B 2034/256; A61B 34/20; A61B 34/25; A61B 5/0022; A61B 5/1118; A61B 5/4509; A61B 5/0402; A61B 5/0476; A61B 5/0488; A61B 5/7475; A61B 5/00; A61N 1/36082;
(Continued)

(56) References Cited

U.S. PATENT DOCUMENTS 7,490,085 B2 * 2/2009 Walker ................... G06F 19/321
7,746,340 B2 * 6/2010 Florin ..................... G06T 15/08
345/420

(Continued)

OTHER PUBLICATIONS

Sutton, Richard S., and Andrew G. Barto. Reinforcement learning: An introduction. vol. 1. No. 1. Cambridge: MIT press, 1998.
(Continued)

*Primary Examiner* — Aklilu Woldemariam

(57) ABSTRACT

A computer-implemented method for identifying an optimal set of parameters for medical image acquisition includes receiving a set of input parameters corresponding to a medical imaging scan of a patient and using a model of operator parameter selection to determine a set of optimal target parameter values for a medical image scanner based on the set of input parameters. The medical imaging scan of the patient is performed using the set of optimal target parameter values to acquire one or more images and feedback is collected from one or more users in response to acquisition of the one or more images. This feedback is used to update the model of operator parameter selection, thereby yielding an updated model of operator parameter selection.

16 Claims, 3 Drawing Sheets

(58) Field of Classification Search
CPC ............ A61N 1/36128; A61N 1/36185; A61N
1/37247; A61N 2005/1058; A61N
2005/1061; A61N 5/1027; G06T
2207/30008; G06T 2207/30016; G06T
2211/424; G06T 2211/436; G06T 7/00;
G06T 7/0014; G06T 2207/10072; G06T
2207/10096; G06T 2207/10108; G06T
2207/10136; G06T 2207/20036; G06T
2207/20064; G06T 2207/20081; G06T
2207/20128; G06T 2207/30004; G06T
2207/30048; G06T 2207/30101; G06T
2207/30104; G06T 2207/30172; G06T
2211/404; G06T 7/0016; G06T 7/17;
G06T 2207/10088; G06T 2207/30012;
G06T 7/11; G06T 7/12; G01R 33/4835;
G01R 33/485; G01R 33/543; G06F
17/3028; G06F 19/321; G06F 3/0484;
G06F 19/3443; G06K 9/34; G06N
99/005; Y10S 7/99943; Y10S 7/99945
USPC ........ 382/128, 129, 130, 131, 132; 600/408,
600/476, 7
See application file for complete search history.

(56) References Cited

U.S. PATENT DOCUMENTS

| | | | |
|---|---|---|---|
| 8,160,357 B2* | 4/2012 | Akinyemi | G06T 7/11 |
| | | | 128/922 |
| 9,760,690 B1* | 9/2017 | Petkov | G06F 19/345 |
| 2005/0267348 A1 | 12/2005 | Wollenweber et al. | |
| 2007/0203871 A1 | 8/2007 | Tesauro et al. | |
| 2008/0267471 A1* | 10/2008 | Yu | G06K 9/4604 |
| | | | 382/128 |
| 2009/0014015 A1* | 1/2009 | Tutar | A61N 5/1027 |
| | | | 128/898 |
| 2009/0099985 A1 | 4/2009 | Tesauro et al. | |
| 2009/0287271 A1* | 11/2009 | Blum | A61N 1/37247 |
| | | | 607/45 |
| 2011/0058719 A1* | 3/2011 | Trzasko | G06T 11/006 |
| | | | 382/131 |
| 2011/0255761 A1* | 10/2011 | O'Dell | G06T 7/0014 |
| | | | 382/131 |
| 2012/0027272 A1* | 2/2012 | Akinyemi | G06T 7/11 |
| | | | 382/128 |
| 2013/0141092 A1 | 6/2013 | Flammang et al. | |
| 2014/0294276 A1* | 10/2014 | Song | G06T 7/0046 |
| | | | 382/132 |
| 2015/0100572 A1* | 4/2015 | Kalafut | G06Q 50/24 |
| | | | 707/736 |
| 2015/0112182 A1* | 4/2015 | Sharma | A61B 5/0261 |
| | | | 600/408 |
| 2015/0141813 A1* | 5/2015 | Kalafut | A61B 6/032 |
| | | | 600/425 |
| 2015/0199478 A1* | 7/2015 | Bhatia | A61B 6/488 |
| | | | 382/128 |
| 2015/0320385 A1* | 11/2015 | Wright | A61B 5/0091 |
| | | | 600/474 |
| 2016/0166333 A1* | 6/2016 | Wang | A61B 34/10 |
| | | | 600/476 |
| 2016/0306924 A1* | 10/2016 | Singh | G06F 19/321 |
| 2017/0103532 A1* | 4/2017 | Ghesu | G06T 7/0012 |

OTHER PUBLICATIONS

Mnih, Volodymyr, et al. "Human-level control through deep reinforcement learning." Nature 518.7540 (2015): 529-533.

Bengio, Yoshua, Aaron C. Courville, and Pascal Vincent. "Unsupervised feature learning and deep learning: A review and new perspectives." CoRR, abs/1206.5538 1 (2012).

Extended European Search Report for corresponding Application No. EP 17183786, dated Oct. 26, 2017.

* cited by examiner

MEDICAL SCANNER TEACHES ITSELF TO OPTIMIZE CLINICAL PROTOCOLS AND IMAGE ACQUISITION

TECHNICAL FIELD

The present invention relates generally to methods, systems, and apparatuses associated with a medical scanner that teaches itself to optimize image acquisition using a machine learning framework. The disclosed methods, systems, and apparatuses may be applied to scanners for any imaging modality.

BACKGROUND

Ensuring highly optimized image acquisitions is one of the key factors for accurate clinical diagnosis in healthcare. However, medical scanning depends on many input parameters such as image information (e.g., quality requirements), patient information (e.g., target organ), clinical protocol (e.g., scan duration), contrast medium utilized, and various scanner parameters. Collectively these parameters represent a complex parameter space that is often difficult to navigate in order to determine an optimal set of input parameters. As a result, parameter selection can be a time intensive process as an operator must explore different parameter combinations in order to achieve desired results. Moreover, many imaging tasks require a set of parameters that are individualized for the study being performed. As a result, even when an optimal set of parameters can be learned for one study, those parameters cannot be easily reused for other, dissimilar studies. Accordingly, it is desired to provide techniques for automating parameter value selection that can be utilized across a large number of imaging applications with minimal input from the operator.

SUMMARY

Embodiments of the present invention address and overcome one or more of the above shortcomings and drawbacks, by providing methods, systems, and apparatuses related to a medical scanner that teaches itself to optimize image acquisition. The techniques described herein facilitate the intelligent optimization of medical image acquisitions using machine learning principles (e.g., executing a deep reinforcement learning framework). To optimize the image acquisition, these techniques make extensive use of any kind of available parameters including, for example, those parameters collected and stored in database systems typically coupled to medical scanners. According to some embodiments, an agent can observe the state of the environment and choose to act on the state, similar to a trial-and-error search, maximizing the future reward signal received as a response from the environment. The environment may be modeled by simulation or operators which gives positive and negative rewards to the current state.

According to some embodiments, a computer-implemented method for identifying an optimal set of parameters for medical image acquisition includes receiving a set of input parameters corresponding to a medical imaging scan of a patient, and using a model of operator parameter selection to determine a set of optimal target parameter values for a medical image scanner based on the set of input parameters. Once generated, these optimal target parameter values may be validated using predetermined limits associated with the medical image scanner. A medical imaging scan of the patient may be performed using these optimal target parameter values to acquire one or more images. Then, feedback may be collected from users (e.g., an indication of acceptance or rejection of the acquired images). This feedback can then be used to further refine the model.

Some embodiments of the aforementioned method further include receiving an additional set of input parameters corresponding to an additional medical imaging scan of the patient (or an additional patient) and determining an additional set of optimal target parameter values using the updated model of operator parameter selection. The additional medical imaging scan of the patient may then be performed using the additional set of optimal target parameter values to acquire one or more additional images.

In some embodiments of the aforementioned method, the model of operator parameter selection is a deep reinforcement learning model utilizing a reward system which provides positive reinforcement for combinations of parameter values yielding one or more target states. This model may be trained, for example, by receiving user inputs collected by remote medical image scanners, creating one or more new target states based on those user inputs, and updating the reward system accordingly. In some embodiments, the input parameters include an indication of an operator utilizing medical imaging scanner and the model is individualized for the operator. Alternatively (or additionally), the input parameters may include an indication of a medical facility utilizing medical imaging scanner and the model is individualized for the medical facility.

According to another aspect of the present invention, as described in various embodiments, a second computer-implemented method for identifying an optimal set of parameters for medical image acquisition includes specifying available parameters for acquiring an image using a medical image scanner and determining a set of actions, with each action specifying a modification of values corresponding to the available parameters. At least one target state is determined using a simulation of the medical image scanner. In some embodiments, this target state comprises estimated target parameter values determined by the simulation of the medical image scanner and the state space is defined by distinct combinations of values corresponding to the plurality of available parameters. Once the target state is determined, a reward system is established based on each action of the set of actions and based on the target state. Next, an artificial agent learns an optimal action-value function approximator specifying behavior of the artificial agent to maximize a cumulative future reward value of the reward system. The behavior of the artificial agent in this example is a sequence of actions moving the artificial agent through a state space towards the target state. The artificial agent may then be used to automatically determine a set of optimal target parameter values based on a set of input target parameters. For example, in some embodiments, the input target parameters comprise an indication of an operator utilizing medical imaging scanner and the reward system is individualized for the operator. In other embodiments, the input target parameters comprise an indication of a medical facility utilizing medical imaging scanner and the reward system is individualized for the medical facility.

The reward system used in the aforementioned second method may be configured in various ways. For example, in some embodiments, the reward system outputs positive reward values if a current state from the state space is proximity to the target state and negative reward values if the current state is divergent from the target state. In other embodiments, the reward system outputs reward values which are inversely proportional to cumulative differences between the estimated target parameter values and parameter values in a current state from the state space. In some embodiments, the reward system is adjusted to provide negative reinforcement for any action in the set of actions which results in a state with parameter values exceeding predetermined limits associated with the medical image scanner. Additionally (or alternatively), the optimal target parameter values may be validated using predetermined limits associated with the medical image scanner.

In some embodiments of the aforementioned second method, the artificial agent learns the optimal action-value function approximator by observing user inputs to the medical image scanner, creating one or more new target states based on those user inputs, and updating the reward system based on the one or more new target states. These user inputs may include, for example, at least one scan performed on the medical image scanner and an indication of acceptance or rejection of the resultant image. In some embodiments, learning of the optimal action-value function approximator further comprises creating new target states based on user inputs collected by remote medical image scanners and updating the reward system based on those new target states.

According to other embodiments of the present invention, a system for identifying an optimal set of parameters for medical image acquisition includes one or more processors, a database, and a non-transitory, computer-readable storage medium in operable communication with the one or more processors. The database is configured to store available parameters for acquiring an image using a medical image scanner and at least one target state related to a medical imaging scanner. The computer-readable storage medium contains programming instructions that, when executed, cause the processors to establish a reward system based on the target state and actions which modify the available parameters. The programming instructions additionally cause an artificial agent to learn an optimal action-value function approximator which specifies behaviors that the artificial agent should use to maximize a cumulative future reward value of the reward system. Each behavior is a sequence of actions that move the artificial agent through a state space towards the target state. Once the approximator is learned, the artificial agent may be used to automatically determine optimal target parameter values based on input target parameters.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures.

DETAILED DESCRIPTION

Figure 1:
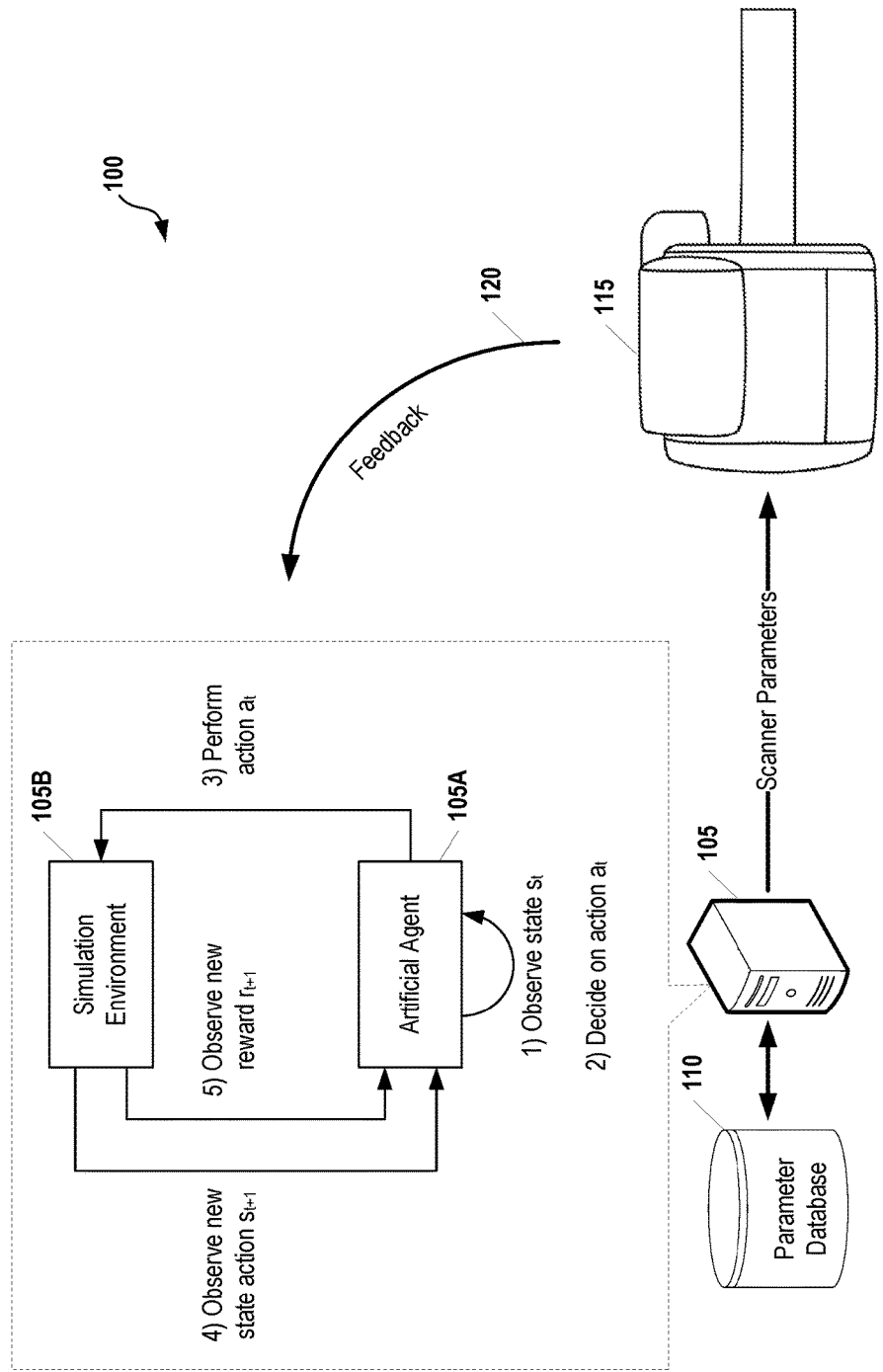
FIG. 1 provides a high-level view of a system which illustrates how an artificial agent may apply deep reinforcement learning to select parameters for use in performing a medical image acquisition, according to some embodiments.

Systems, methods, and apparatuses are described herein which relate generally to various techniques related to a self-teaching system for medical scanners which automatically learns to optimize image acquisition. More specifically, the techniques described herein optimize image acquisition on medical scanners using self-teaching models of operator parameter selection which exploit parameters available, for example, locally on the scanner or in a connected database. The collected parameters may include, for example, image data, patient data, attributes from the clinical protocol and scanner parameters, and configurations. The examples provided herein describe the techniques in the context of a deep reinforcement learning framework, where an intelligent agent identifies relevant features from a pool of attributes and then derives actions to automatically converge to a target parameter setting. However, the general approach described herein may be extended to other forms of machine learning (e.g., artificial neural networks). The end result is an optimized image acquisition which minimizes scanning time, results in lower radiation, and improves image quality in comparison to conventional techniques.

Deep Reinforcement Learning

Deep reinforcement learning (DRIL) techniques are used to generate intelligence of the artificial agent of the disclosed embodiments, allowing the artificial agent to learn (e.g., optimize behavior). General deep learning techniques are conventionally applied to various problems ranging from image classification, object detection and segmentation, and speech recognition to transfer learning. Deep learning is the automatic learning of hierarchical data representations describing the underlying phenomenon. That is, deep learning proposes an automated feature design by extracting and disentangling data-describing attributes directly from the raw input in contrast to feature handcrafting. Hierarchical structures encoded by neural networks are used to model this learning approach.

The convolutional neural network (CNN) mimics non-cyclic, feed-forward type of information processing observable in the early visual cortex. This learning emulates, automates, and improves the principles of animal and human receptive fields. Deep fully connected neural networks include multiple layers. Each layer learns a more abstract and insightful data representation using the output from the previous layer. Hierarchical layers of translation-invariant convolutional filter kernels are constructed based on local spatial correlations observable in images.

The application of the filter kernel to the data generates a representation of the filtered data at each layer, called a representation map. The representation map generated by the l-th convolutional filter kernel in the layer k by $\vec{\omega}^{(k,l)}$, is represented by Equation 1:

$$o_{i,j} = \sigma((\vec{\omega}^{(k,l)} * \vec{x})_{i,j} + b^{(k,l)}) \qquad \text{Eq. 1}$$

where x is the representation map from the previous layer used as input for the l-th convolutional filter kernel, (i, j) defines the evaluation location of the filter and $b^{(k,l)}$ is the bias of the considered output neuron. The function a represents the activation function used to synthesize the input information. Possible alternatives to the above activation function may be selected based on the given learning problems. Examples of learning problems include classification, multi-class classification or regression, and example alternative functions include the sigmoid function, hyperbolic tangent, or rectified linear units (ReLU).

Given a set of scalar or matrix data of independent observations "•", such as input patches $\vec{X}$, and corresponding value assignments $\vec{y}$, the network response function may be defined as $R(\bullet; \vec{\omega}, \vec{b})$. Thus, a Maximum Likelihood Estimation to estimate the optimal parameters for the CNN results as Equation 2:

$$\vec{\omega}, \vec{b} = \arg_{\vec{\omega}, \vec{b}}{}^{max} L(\vec{\omega}, \vec{b}) = \arg_{\vec{\omega}, \vec{b}}{}^{min} \|R(\vec{X}; \vec{\omega}, \vec{b}) - \vec{y}\|_2^2 \qquad \text{Eq. 2}$$

The optimization may be solved with the Stochastic Gradient Descent (SGD) method or rms-prop in a mini-batch approach. Using a random set of samples $\tilde{X}$ from the training input, a feed-forward propagation is performed to compute the network response $R(\vec{X}; \vec{\omega}, \vec{b})$. Denoting $\vec{\omega}(t)$ and $\vec{b}(t)$, the network parameters in the t-th optimization step are updated according to Equation 3:

$$\vec{\omega}(t+1) = \vec{\omega}(t) - n\nabla_\omega E(\tilde{X}; \vec{\omega}(t), \vec{b}(t)) \qquad \text{Eq. 3}$$

$$\vec{b}(t+1) = \vec{b}(t) - n\nabla_b E(\tilde{X}; \vec{\omega}(t), \vec{b}(t)),$$

where $\nabla$ is the gradient of the cost function with respect to the network parameters, n the magnitude of the update. That is, the learning rate, and $E(\tilde{X}: \vec{\omega}(t), \vec{b}(t)) = \|R(\vec{X}; \vec{\omega}, \vec{b}) - \vec{y}\|_2^2$ represents the error function. Backpropagation may be used to compute and apply the gradient to the network parameters.

The disclosed embodiments use deep learning in conjunction with Reinforcement Learning (RL). RL facilitates learning as an end-to-end cognitive process for an artificial agent, instead of a predefined methodology. One RL setting is composed by an artificial agent that can interact with an uncertain environment (e.g., a request to acquire image data with limited or no parameters) with the target of reaching pre-determined goals (e.g., acquiring the image with the optimal parameters). The agent can observe the state of the environment and choose to act on the state, similar to a trial-and-error search, maximizing the future reward signal received as a response from the environment. The environment may be modeled by simulation or operators which gives positive and negative rewards to the current state.

An optimal action-value function approximator Q* estimates the agent's response to an image acquisition parameterized by state space $s_t$. in the context of a reward function $r_t$. This reward-based decision process is modeled in RL theory as a Markov Decision Process (MDP) defined by a tuple $M:=S, A, T, R, \gamma$, where S is a finite set of states and $S_t \in S$ is the state of the agent at time t. A is a finite set of actions allowing the agent to interact with the environment, and $a_t \in A$ is the action the agent performs at time t. $T: S \times A \times S \to [0; 1]$ is a stochastic transition function, where $T_{s,a}^{s'}$ is the probability of arriving in state s' after the agent performed action a in state s. $R: S \times A \times S \to \mathbb{R}$ is a scalar reward function, where $R_{s,a}^{s'}$ is the expected reward after a state transition. $\gamma$ is the discount factor controlling the importance of future versus immediate rewards.

The future discounted reward of an agent at time $\hat{t}$ can be written as $R_{\hat{t}} = \Sigma_{t=\hat{t}}^T \gamma^{t-\hat{t}} r_t$, with T marking the end of a learning episode and $r_t$ defining the immediate reward the agent receives at time t. In model-free reinforcement learning, the target may be to find the optimal so called "action-value function," which denotes the maximum expected future discounted reward when starting in state s and performing action a as in Equation 4:

$$Q^*(s,a) = \max_\pi \mathbb{E}[R_t | s_t = s, a_t = a, \pi] \qquad \text{Eq. 4}$$

where $\pi$ is an action policy. That is, the action policy is a probability distribution over possible actions in each given state. Once the optimal action-value function is estimated, an optimal action policy determining the behavior of the agent can be directly computed in each state as shown in Equation 5:

$$\forall_s \in S: \pi^*(s) = \text{argmax}_{a \in A} Q^*(s,a) \qquad \text{Eq. 5}$$

The optimal action-value function approximator Q* is the Bellman optimality equation, representing a recursive formulation of Equation 4, defined as Equation 6:

$$Q^*(s,a) = \Sigma_{s'} T_{s,a}^{s'}(R_{s,a}^{s'} + \gamma \max_{a'} Q^*(s', a')) \qquad \text{Eq. 6}$$

where s' defines a possible state visited after s, a' the corresponding action and $r = R_{s,a}^{s'}$ represents a compact notation for the current, immediate reward. Viewed as an operator $\tau$, the Bellman equation defines a contraction mapping. Applying $Q_{i+1} = \tau(Q_i)$, $\forall(s, a)$, the function $Q_i$ converges to Q* at infinity. This standard, model-based policy iteration approach is, however, not feasible in practice. An alternative is the use of model-free temporal difference methods, typically Q-Learning, which exploits correlation of consecutive states, is more applicable in practice. Using parametric functions to approximate the Q-function furthers a goal of higher computational efficiency. Considering the expected non-linear structure of the action-value function, neural networks represent a sufficiently powerful approximation solution.

System Operation

FIG. 1 provides a high-level view of a system 100 which illustrates how an Artificial Agent 105A may apply deep reinforcement learning to select parameters for use in performing a medical image acquisition, according to some embodiments. Briefly, the system 100 includes a Parameter Selection Computer 105, a Parameter Database 110, and a Medical Imaging Scanner 115. In this example, the Medical Imaging Scanner 115 is a magnetic resonance imaging (MRI) scanner however, in principle, any type of image scanner may be used. The Parameter Selection Computer 105 retrieves parameter information from the Parameter Database 110. Based on the retrieved parameters, an Artificial Agent 105A learns an optimal action-value function approximator specifying behavior of the Artificial Agent 105A to maximize a cumulative future reward value of the reward system. The rewards in this example are defined using a Simulation Environment 105B which simulates the operation of the Medical Imaging Scanner 115. Thus, using the Simulation Environment 105B, the Artificial Agent 105A can explore the parameter space and generate rewards for various combinations of parameters. Once the Artificial Agent 105A is fully trained, it may be used to automatically determine a set of optimal target parameter values based on a set of input target parameters. These optimal target parameter values may then be used to perform a scan on the Medical Imaging Scanner 115. After the scan the operator or examiners may provide feedback 120 regarding the optimal target parameter values to the Parameter Selection Computer 105. The Parameter Selection Computer 105 may then use this feedback to further refine the reward system employed by the Artificial Agent 105A.

The general process illustrated in FIG. 1 can be applied to automatic selection of parameters for medical image acquisitions, regardless of the modality involved (e.g., for computed tomography, magnetic resonance, ultrasound, x-ray, molecular, or other modalities). In this formulation, the environment is encoded and defined by the current image acquisition strategy. An example would be where the model for the image acquisition strategy may be defined by parameters extracted from the database and is targeting to map a certain organ of a patient with a defined dose within a maximum timeframe. The system automatically teaches itself to meet these parameters by adaption of various parameters.

The Artificial Agent 105A functions primarily in two phases: training and testing. In the training phase, the agent learns to optimize its selection of its actions based on pre-defined parameter settings generated via an idealized model of the medical image scanner. In the testing phase, medical imaging tasks are input and the agent selects a set of parameters in the manner learned by the agent during the training phase. The Artificial Agent 105A is generated and trained to self-develop an optimized method for efficiently selecting parameters for an image acquisition. In some embodiments, the Artificial Agent 105A may be trained, for example, using root mean square (RMS)-prop mini-batch or stochastic gradient descent techniques.

Although the Parameter Database 110 may include any number of parameters, these parameters may generally be classified into the following categories: image information, patient information, clinical protocol, contrast medium, and various scanner parameters. The table below summarizes examples of parameters that may be included in each of these categories:

movement that occurs during state space transitions with respect to the state space's proximity to the optimal set of parameters.

In order to learn optimal action policy in a sequence of learning episodes, the agent is given random parameter start-states. For each state s, there are a set of actions A which result in a change to the parameters (i.e., a change of one or more parameters in the current state $s_t$). The set A of actions include all the available changes in the parameters from the current state $s_t$. The initial parameter state may be a random selection of the available parameters or, alternatively, a set of pre-selected parameters (e.g., the most frequently used parameter settings). The action $a_t$ modifies one or more of the parameters in the current state $s_t$ to generate a new state $s_{t+1}$. Once the new state $s_{t+1}$ is generated, it is used as input into the Simulation Environment 105B which performs a simulated image acquisition using the corresponding parameters. The agent then follows a $\epsilon$-greedy search strategy over the parameter space to generate a set of parameters which are added to its experience memory. During exploration, periodic updates are applied to the parameters of the neural network, leading to a more accurate approximation of the optimal Q* function, given the current experience. This process is repeated in an iterative manner until the detection accuracy on the validation set is minimal.

Figure 2:
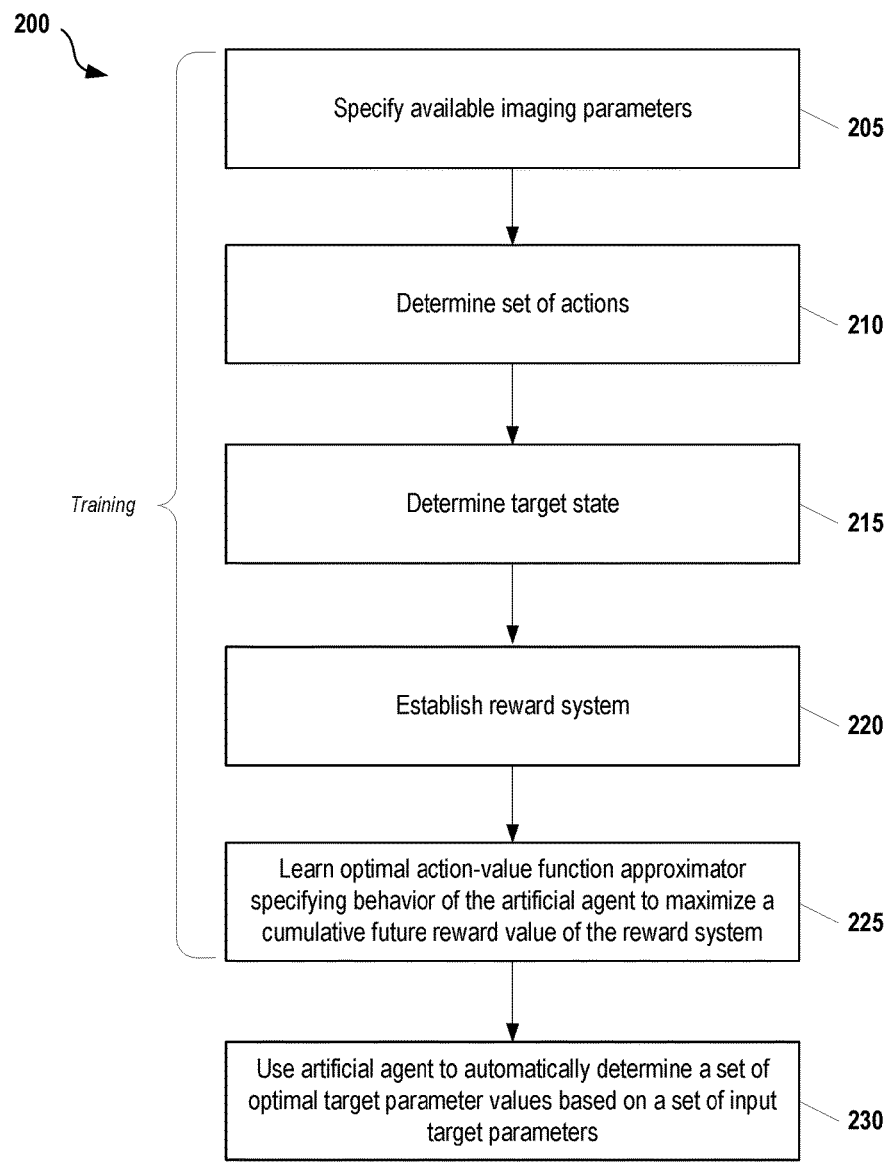
FIG. 2 illustrates a method for identifying an optimal set of parameters for medical image acquisition, according to some embodiments.

FIG. 2 illustrates a method 200 for identifying an optimal set of parameters for medical image acquisition, according to some embodiments. Starting at step 205, a plurality of available parameters for acquiring an image using a medical image scanner is specified. In some embodiments, these parameters are stored in a database indexed according to scanner type. Thus, during execution of the method 200, the

| Image information | Patient information | Clinical protocol | Contrast medium | Scanner parameters |
|---|---|---|---|---|
| quality | target organ | scan duration | iodine mass rate, saline flush | geometry sampling scheme |
| artefacts | weight | scan delays | | |
| content | height | multi-phase scan | injection duration | pre-filtration |
| quantification adequacy | cardiac output age/gender breath holding renal function | | injection pattern | x-ray spectral calibration reconstruction |

It should be noted that the parameters set forth in this table are merely examples of the parameter space that may be utilized and, in some embodiments, additional parameters may be included to increase the robustness of the system. The consideration of this huge parameter space by hand may make optimal image acquisition challenging, as the scanning may result in a sort of "local optimally" image acquisition. Thus, the Artificial Agent 105A applies deep reinforcement learning to converge to an optimized solution by balancing exploration and data exploitation.

The Artificial Agent 105A begins by randomly navigating through the parameter space and uses a simulation of the medical imaging scanner to generate simulated images with different parameter combinations. Gradually, the agent learns a policy during training to optimize the expected reward value rt of its actions. Expected rewards are determined by the reward value of the possible actions, a, available to the agent at time, t with the goal of identifying the optimal set of parameters for generating an image (via maximizing expected reward value). Actions, a, define the parameter space can be limited to a particular imaging modality or even a particular scanner model. At step 210, a set of actions are determined. Each action specifies a modification of values corresponding to the plurality of available parameters. The modification may be performed, for example, by randomly selecting parameter values within predetermined limits corresponding to each particular parameter.

Continuing with reference to FIG. 2, at step 215, at least one target state is determined using a simulation of the medical image scanner. Each target state includes a set of parameters values estimated by the simulation to represent an optimal input to the medical scanner for a given set of conditions. The exact implementation of the simulation may vary; however, in general, any simulation of the scanner maybe employed at step 215. Ideally, the simulation should provide a high-fidelity modeling of scanner hardware under a variety of conditions to ensure that the state space is fully explored when selecting the target state.

At step 220, a reward system is established based on each action of the set of actions and based on the target state. The exact implementation of the reward system may vary across different embodiments of the present invention. For example, in some embodiments, reward system may output the positive reward values if a current state from the state space is proximity to the target state (e.g., based on differences in values between each applicable input parameter). Conversely, the reward system may output negative reward values if the current state is divergent from the target state. Alternatively, in other embodiments, the reward system outputs reward values which are inversely proportional to cumulative differences between the estimated target parameter values and parameter values in a current state from the state space.

In some embodiments, the reward system may be adjusted to provide negative reinforcement for any action which results in a state with parameter values exceeding predetermined limits associated with the medical image scanner or medical procedure. This negative reinforcement ensures that parameter values will not be selected which are harmful to the patient or scanner equipment. For example, in the context of a CT scanner, the negative reinforcement ensures that the patient will not be exposed to a high dosage or the scanner parameters will not damage the scanner hardware. For patient information, the predetermined limits used for creating the negative reinforcement may be set based on, for example, information from medical studies or other known biological standard information. The limits associated with the scanner equipment may be set based on manufacture specifications or other known information about the hardware. This general concept may also be extended to consider additional concepts that may be of interest to the facility operating the scanner. For example, if the facility has a goal of reducing the overall power consumption for scanners used throughout the facility, a negative reinforcement may be created for sets of parameter values that entail comparatively high levels of power to implement.

Returning to FIG. 2, at step 225, an artificial agent learns an optimal action-value function approximator specifying behavior of the artificial agent to maximize a cumulative future reward value of the reward system, wherein the behavior of the artificial agent is a sequence of actions moving the artificial agent through a through a state space towards the at least one target state. The state space in this case is defined by distinct combinations of values corresponding to the plurality of available parameters. In some embodiments, the artificial agent may learn the optimal action-value function approximator based on real world user interactions with the medical image scanner. For example, in one embodiment, the artificial agent learns the approximator by observing user inputs to the medical image scanner are collected (e.g., either through direct or indirect observation). These inputs are used to create new target states based on the user input and update the reward system based on the one or more new target states. The user inputs may include, for example, input data from scan performed on the medical image scanner and an indication of acceptance or rejection of a resultant image. Additionally, this concept can be extended to remote medical scanners (e.g., in different hospitals) to allow the reward system to be updated based on scanner usage across a large population of users.

At step 230, the artificial agent is used to automatically determine a set of optimal target parameter values based on a set of input target parameters. In some embodiments, this set of input target parameters comprises an indication of an operator utilizing medical imaging scanner and the reward system is individualized for the operator. Similarly, the input target parameters may be defined across the medical facility (e.g., hospital) and the reward system is individualized for the facility.

Once the optimal target parameter values have been determined, a validation may be performed using predetermined limits associated with the medical image scanner or the medical procedure generally. This process is similar to the adjustment of the reward system described above with respect to step 220. The goal of the validation is confirming that the optimal target parameter values are not harmful to the scanner hardware or patient. If the validation is successful, the optimal target parameter values may then be used to perform the scan. Alternatively, if the optimal target parameter values exceed any of the pre-determined limits, they may be discarded and new values can be computed.

The techniques described herein can be applied to any type of medical scanner (e.g., Computed Tomography, Magnetic Resonance, Ultrasound, X-ray, PET, etc.) where image acquisition is performed based on many input parameters. Optimal settings are learned by the system automatically. The self-learning strategy based on deep reinforcement learning identifies hierarchies and dependencies in the parameter space and exploits it towards optimal image acquisition without external inputs. The techniques may be also applied to perform behavioral learning by observing an expert during image acquisition. For example, parameter settings may be collected that provide an optimal image acquisition and may learn from these observations to create the rewards and efficient strategy for improved convergence to optimal strategy.

Figure 3:
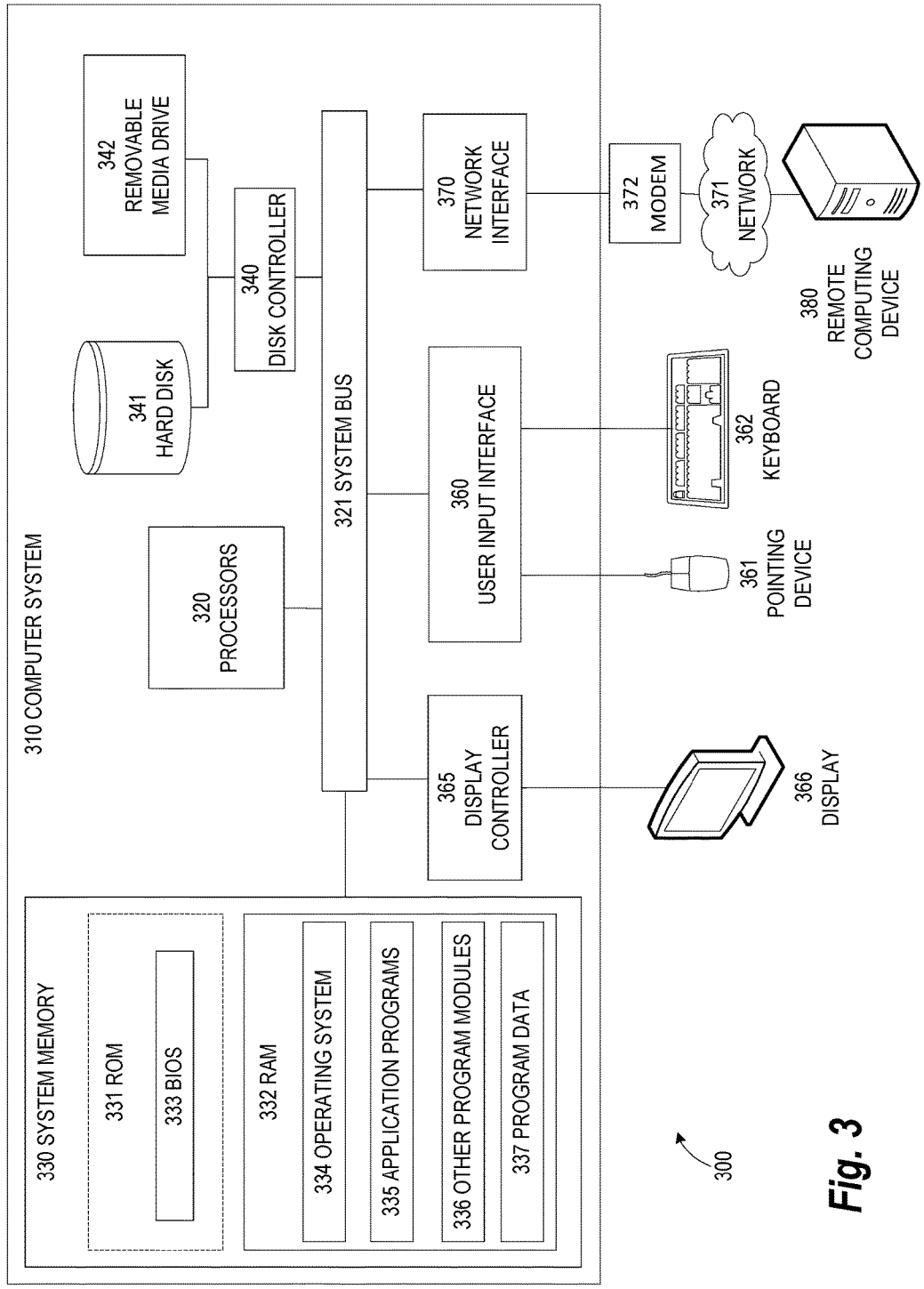
FIG. 3 illustrates an exemplary computing environment within which embodiments of the invention may be implemented.

FIG. 3 illustrates an exemplary computing environment 300 within which embodiments of the invention may be implemented. For example, this computing environment 300 may be used to implement the method 200 described above with respect to FIG. 2. In some embodiments, the computing environment 300 may be used to implement one or more of the components illustrated in the system 100 of FIG. 1. The computing environment 300 may include computer system 310, which is one example of a computing system upon which embodiments of the invention may be implemented. Computers and computing environments, such as computer system 310 and computing environment 300, are known to those of skill in the art and thus are described briefly here.

As shown in FIG. 3, the computer system 310 may include a communication mechanism such as a bus 321 or other communication mechanism for communicating information within the computer system 310. The computer system 310 further includes one or more processors 320 coupled with the bus 321 for processing the information. The processors 320 may include one or more central processing units (CPUs), graphical processing units (GPUs), or any other processor known in the art.

The computer system 310 also includes a system memory 330 coupled to the bus 321 for storing information and instructions to be executed by processors 320. The system memory 330 may include computer readable storage media in the form of volatile and/or nonvolatile memory, such as read only memory (ROM) 331 and/or random access memory (RAM) 332. The system memory RAM 332 may include other dynamic storage device(s) (e.g., dynamic RAM, static RAM, and synchronous DRAM). The system memory ROM 331 may include other static storage device(s) (e.g., programmable ROM, erasable PROM, and electrically erasable PROM). In addition, the system memory 330 may be used for storing temporary variables or other intermediate information during the execution of instructions by the processors 320. A basic input/output system (BIOS) 333 containing the basic routines that help to transfer information between elements within computer system 310, such as during start-up, may be stored in ROM 331. RAM 332 may contain data and/or program modules that are immediately accessible to and/or presently being operated on by the processors 320. System memory 330 may additionally include, for example, operating system 334, application programs 335, other program modules 336 and program data 337.

The computer system 310 also includes a disk controller 340 coupled to the bus 321 to control one or more storage devices for storing information and instructions, such as a hard disk 341 and a removable media drive 342 (e.g., floppy disk drive, compact disc drive, tape drive, and/or solid state drive). The storage devices may be added to the computer system 310 using an appropriate device interface (e.g., a small computer system interface (SCSI), integrated device electronics (IDE), Universal Serial Bus (USB), or FireWire).

The computer system 310 may also include a display controller 365 coupled to the bus 321 to control a display 366, such as a cathode ray tube (CRT) or liquid crystal display (LCD), for displaying information to a computer user. The computer system includes an input interface 360 and one or more input devices, such as a keyboard 362 and a pointing device 361, for interacting with a computer user and providing information to the processor 320. The pointing device 361, for example, may be a mouse, a trackball, or a pointing stick for communicating direction information and command selections to the processor 320 and for controlling cursor movement on the display 366. The display 366 may provide a touch screen interface which allows input to supplement or replace the communication of direction information and command selections by the pointing device 361.

The computer system 310 may perform a portion or all of the processing steps of embodiments of the invention in response to the processors 320 executing one or more sequences of one or more instructions contained in a memory, such as the system memory 330. Such instructions may be read into the system memory 330 from another computer readable medium, such as a hard disk 341 or a removable media drive 342. The hard disk 341 may contain one or more datastores and data files used by embodiments of the present invention. Datastore contents and data files may be encrypted to improve security. The processors 320 may also be employed in a multi-processing arrangement to execute the one or more sequences of instructions contained in system memory 330. In alternative embodiments, hard-wired circuitry may be used in place of or in combination with software instructions. Thus, embodiments are not limited to any specific combination of hardware circuitry and software.

As stated above, the computer system 310 may include at least one computer readable medium or memory for holding instructions programmed according to embodiments of the invention and for containing data structures, tables, records, or other data described herein. The term "computer readable medium" as used herein refers to any medium that participates in providing instructions to the processor 320 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 341 or removable media drive 342. Non-limiting examples of volatile media include dynamic memory, such as system memory 330. Non-limiting examples of transmission media include coaxial cables, copper wire, and fiber optics, including the wires that make up the bus 321. Transmission media may also take the form of acoustic or light waves, such as those generated during radio wave and infrared data communications.

The computing environment 300 may further include the computer system 310 operating in a networked environment using logical connections to one or more remote computers, such as remote computer 380. Remote computer 380 may be a personal computer (laptop or desktop), a mobile device, a server, a router, a network PC, a peer device or other common network node, and typically includes many or all of the elements described above relative to computer system 310. When used in a networking environment, computer system 310 may include modem 372 for establishing communications over a network 371, such as the Internet. Modem 372 may be connected to bus 321 via user network interface 370, or via another appropriate mechanism.

Network 371 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 310 and other computers (e.g., remote computer 380). The network 371 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 371.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

The invention claimed is:

1. A computer-implemented method for identifying an optimal set of parameters for medical image acquisition, the method comprising:
    receiving a set of input parameters corresponding to a medical imaging scan of a patient;
    using a model of operator parameter selection to determine a set of optimal target parameter values for a medical image scanner based on the set of input parameters, wherein the model of operator parameter selection is a deep reinforcement learning model utilizing a reward system which provides positive reinforcement for combinations of parameter values yielding one or more target states;
    performing the medical imaging scan of the patient using the set of optimal target parameter values to acquire one or more images;
    collecting feedback from one or more users in response to acquisition of the one or more images, wherein the feedback from the one or more users comprises an indication of acceptance or rejection of the one or more images; and
    using the feedback to update the target states used by the model of operator parameter selection, thereby yielding an updated model of operator parameter selection,
    wherein the reward system outputs reward values which are inversely proportional to cumulative differences between the estimated target parameter values and parameter values in a current state from the state space.

2. The method of claim 1, further comprising:
    receiving an additional set of input parameters corresponding to an additional medical imaging scan of the patient or an additional patient;
    determining an additional set of optimal target parameter values based on the additional set of input parameters using the updated model of operator parameter selection; and
    performing the additional medical imaging scan of the patient or the additional patient using the additional set of optimal target parameter values to acquire one or more additional images.

3. The method of claim 1, wherein the deep reinforcement learning model is trained by a process comprising:
    receiving a plurality of user inputs collected by remote medical image scanners;
    creating one or more new target states based on the plurality of user inputs; and
    updating the reward system based on the one or more new target states.

4. The method of claim 1, wherein the set of input parameters comprises an indication of an operator utilizing medical imaging scanner and the model of operator parameter selection is individualized for the operator.

5. The method of claim 1, wherein the set of input parameters comprises an indication of a medical facility utilizing medical imaging scanner and the model of operator parameter selection is individualized for the medical facility.

6. The method of claim 1, further comprising:
    performing a validation of the set of optimal target parameter values using predetermined limits associated with the medical image scanner.

7. A computer-implemented method for identifying an optimal set of parameters for medical image acquisition, the method comprising:
    specifying a plurality of available parameters for acquiring an image using a medical image scanner;
    determining a set of actions, each action specifying a modification of values corresponding to the plurality of available parameters;
    determining at least one target state using a simulation of the medical image scanner;
    establishing a reward system based on each action of the set of actions and based on the at least one target state;
    learning, by an artificial agent, an optimal action-value function approximator specifying behavior of the artificial agent to maximize a cumulative future reward value of the reward system, wherein the behavior of the artificial agent is a sequence of actions moving the artificial agent through a through a state space towards the at least one target state; and
    using the artificial agent to automatically determine a set of optimal target parameter values based on a set of input target parameters,
    wherein the at least one target state comprises estimated target parameter values determined by the simulation of the medical image scanner, and wherein the state space is defined by distinct combinations of values corresponding to the plurality of available parameters, and
    wherein the reward system outputs reward values which are inversely proportional to cumulative differences between the estimated target parameter values and parameter values in a current state from the state space.

8. The method of claim 7, wherein the reward system outputs:
    positive reward values if a current state from the state space is proximity to the at least one target state, and negative reward values if the current state is divergent from the at least one target state.

9. The method of claim 7, wherein learning, by the artificial agent, the optimal action-value function approximator specifying the behavior of the artificial agent further comprises:
observing a plurality of user inputs to the medical image scanner;
creating one or more new target states based on the plurality of user inputs; and
updating the reward system based on the one or more new target states.

10. The method of claim 9, wherein the plurality of user inputs comprise at least one scan performed on the medical image scanner and an indication of acceptance or rejection of a resultant image.

11. The method of claim 7, wherein learning, by the artificial agent, an optimal action-value function approximator specifying the behavior of the artificial agent further comprises:
receiving a plurality of user inputs collected by remote medical image scanners;
creating one or more new target states based on the plurality of user inputs; and
updating the reward system based on the one or more new target states.

12. The method of claim 7, wherein the set of input target parameters comprises an indication of an operator utilizing the medical image scanner and the reward system is individualized for the operator.

13. The method of claim 7, wherein the set of input target parameters comprises an indication of a medical facility utilizing medical imaging scanner and the reward system is individualized for the medical facility.

14. The method of claim 7, further comprising:
adjusting the reward system to provide negative reinforcement for any action in the set of actions which results in a state with parameter values exceeding predetermined limits associated with the medical image scanner.

15. The method of claim 7, further comprising:
performing a validation of the set of optimal target parameter values using predetermined limits associated with the medical image scanner.

16. A system for identifying an optimal set of parameters for medical image acquisition, the system comprising:
one or more processors;
a database configured to store:
a plurality of available parameters for acquiring an image using a medical image scanner, and
at least one target state related to a medical imaging scanner; and
a non-transitory, computer-readable storage medium in operable communication with the one or more processors, wherein the computer-readable storage medium contains one or more programming instructions that, when executed, cause the processors to:
determine a set of actions, each action specifying a modification of values corresponding to the plurality of available parameters,
establish a reward system based on each action of the set of actions and based on the at least one target state,
learn, by an artificial agent, an optimal action-value function approximator specifying behavior of the artificial agent to maximize a cumulative future reward value of the reward system, wherein the behavior of the artificial agent is a sequence of actions moving the artificial agent through a through a state space towards the at least one target state, and
use the artificial agent to automatically determine a set of optimal target parameter values based on a set of input target parameters,
wherein the reward system outputs reward values which are inversely proportional to cumulative differences between the estimated target parameter values and parameter values in a current state from the state space.

* * * * *